United States Patent [19]

Susuki

[11] Patent Number: 4,779,468
[45] Date of Patent: Oct. 25, 1988

[54] HUMID-ENVIRONMENTAL TESTING APPARATUS FOR DETERMINING CORROSION-RESISTANCE OF SELF-PROPELLED VEHICLE

[75] Inventor: Teruaki Susuki, Yachiyo, Japan

[73] Assignee: Kabushiki-Kaisha Toyo Seisakusho, Tokyo, Japan

[21] Appl. No.: 25,097

[22] Filed: Mar. 12, 1987

[51] Int. Cl.$^4$ .......................................... G01N 17/00
[52] U.S. Cl. .................................................. 73/865.6
[58] Field of Search ........................ 73/865.6, 117.1; 236/1 R, 44 R, 44 A

[56] References Cited

U.S. PATENT DOCUMENTS

| H229 | 3/1987 | Phillips | 73/865.6 |
|---|---|---|---|
| 1,465,028 | 8/1923 | Stacey, Jr. | 236/44 R |
| 2,471,733 | 5/1949 | Fiduccia . | |
| 2,571,069 | 10/1951 | Shearman . | |
| 2,699,614 | 1/1955 | Welch . | |
| 2,703,488 | 3/1955 | Gevantman et al. | 73/865.6 |
| 2,968,164 | 1/1961 | Hanson . | |
| 3,074,191 | 1/1963 | Zierak . | |
| 3,259,466 | 7/1966 | Jacks, Jr. | 73/865.6 |
| 3,488,681 | 1/1970 | Mita et al. | 73/865.6 |
| 3,508,030 | 4/1970 | Julie | 236/1 |
| 3,521,029 | 7/1970 | Toyooka et al. . | |
| 4,275,833 | 6/1981 | Fairbank . | |
| 4,282,181 | 8/1981 | Pierce | 73/865.6 |
| 4,465,230 | 8/1984 | Ash . | |
| 4,602,503 | 7/1986 | Hile et al. | 73/865.6 |
| 4,667,522 | 5/1987 | Kawahasa | 73/865.6 |

FOREIGN PATENT DOCUMENTS

| 0024548 | 2/1977 | Japan . | |
|---|---|---|---|
| 0158535 | 9/1982 | Japan . | |
| 184943 | 11/1982 | Japan | 73/865.6 |
| 0184945 | 11/1982 | Japan . | |
| 264273 | 2/1970 | U.S.S.R. | 73/865.6 |
| 1083039 | 3/1984 | U.S.S.R. . | |
| 1237876 | 6/1986 | U.S.S.R. . | |

Primary Examiner—Stewart J. Levy
Assistant Examiner—Robert R. Raevis
Attorney, Agent, or Firm—Sandler & Greenblum

[57] ABSTRACT

A humid-environmental testing apparatus for determining a corrosion-resistance of a self-propelled vehicle, comprises: an oblique indoor-ceiling board installed in an upper portion of a main frame of the apparatus; a ceiling duct defined between a ceiling surface of the main frame and the indoor-ceiling board; a testing chamber positioned under the indoor-ceiling board, in which chamber an air-inlet portion of the ceiling duct opens; an air-intake duct provided with an air-conditioning unit, with which air-intake duct is connected an air-outlet portion of the ceiling duct; an air-discharging duct making its air-discharging opening open into the testing chamber, with which air-discharging duct is connected the air-intake duct; and drainage means provided in a lower edge portion of the oblique indoor-ceiling board.

9 Claims, 3 Drawing Sheets 4,779,468

HUMID-ENVIRONMENTAL TESTING APPARATUS FOR DETERMINING CORROSION-RESISTANCE OF SELF-PROPELLED VEHICLE

BACKGROUND OF THE INVENTION

1. Field of the Invention

The present invention relates to a humidity environmental testing apparatus for determining the corrosion-resistance, durability and the like of a self-propelled vehicle, such as an automobile or the like; in this apparatus are produced various environmental conditions, for example, humid-atmospheric conditions having relative humidities of more than 95%, such as a misty atmosphere, a rainy atmosphere and the like, and various wind-velocity conditions and the like to which self-propelled vehicles are subjected.

2. Description of the Prior Art

In a conventional environmental testing apparatus for testing the corrosion-resistance and the durability of the automobile under humid atmospheric conditions, the moisture contained in air confined in the testing apparatus is condensed into water droplets which drop on the automobile, which comprises the article to be tested, thus making it difficult to keep the automobile under accurate humidity conditions. This is a defect in conventional environmental testing apparatus for self-propelled vehicles such as automobiles and the like.

SUMMARY OF THE INVENTION

It is an object of the present invention to protect an article being tested, i.e., an automobile, from moisture-condensed water droplets by employing an oblique indoor-ceiling board which is installed in a main frame of a humid-environmental testing apparatus (hereinafter referred to as the testing apparatus's main frame), which oblique indoor-ceiling board enables the water droplets to flow down along the board and prevents the water droplets from dropping on the automobile.

It is another object of the present invention to effectively utilize the interior space of the testing apparatus's main frame by employing the space which is defined between the indoor ceiling board and a ceiling portion of the testing apparatus's main frame, as a duct.

In order to accomplish these objects of the present invention, according to the present invention, there is provided a humid-environmental testing apparatus for determining the corrosion-resistance of a self-propelled vehicle. The apparatus comprises an oblique indoor-ceiling board installed in an upper portion of a main frame of said testing apparatus; a ceiling duct defined between a ceiling surface of said main frame of the testing apparatus and said oblique indoor-ceiling board; a testing chamber positioned under the oblique indoor-ceiling board in the main frame of the testing apparatus, into which an air-inlet portion of said ceiling duct opens; an air-intake duct provided with an air-conditioning unit, with which the air-intake duct is connected to an air-outlet portion of said ceiling duct; an air-discharging duct having discharged air opening into said testing chamber, with which the air-discharge duct is connected to the air-intake duct; and drainage means provided in a lower edge portion of the oblique indoor-ceiling board.

DESCRIPTION OF THE PREFERRED EMBODIMENTS

Hereinbelow, embodiments of the present invention will be described in detail with reference to the drawings.

Figure 1:
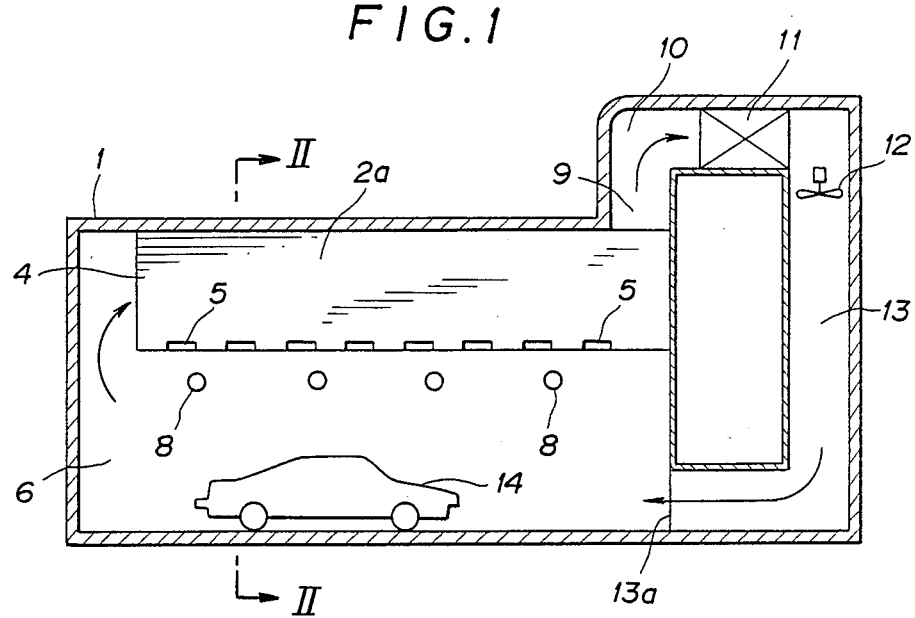
FIG. 1 is a longitudinal sectional view of an embodiment of a humid-environmental testing apparatus of the present invention.
Figure 2:
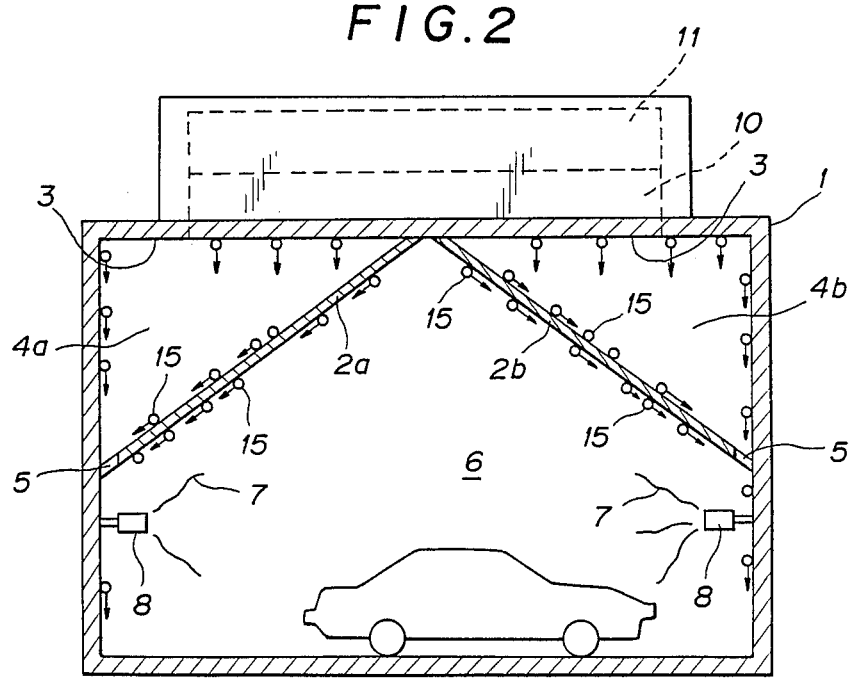
FIG. 2 is an enlarged cross-sectional view of the embodiment, taken along the line II—II of FIG. 1.

As shown in FIGS. 1 and 2, in an upper portion of the interior of a main frame of a humid-environmental testing apparatus, i.e., the testing apparatus's main frame 1, are symmetrically arranged, as viewed in cross-section, oppositely inclined oblique indoor-ceiling boards 2a, 2b, so that ceiling ducts 4a and 4b both of which have triangular shapes, are formed between a ceiling surface 3 of the testing apparatus's main frame 1 and the oblique indoor-ceiling boards 2a and 2b, respectively.

At lower end portions of the oblique indoor-ceiling boards 2a, 2b, that is, at portions of the boards abutting on inner wall surfaces of the testing apparatus's main frame 1, there are provided drainage means such as drainage holes 5 enabling water droplets, which flow along the wall surfaces of the ceiling ducts 4a, 4b, to flow down along an inner wall surface of the testing apparatus's main frame 1.

The reference numeral 6 denotes a testing chamber, in a wall surface of which is provided a nozzle 8 for spraying a mist 7 into the testing chamber 6.

Each of the ceiling ducts 4a, 4b is provided with an air-inlet portion 4 at its front end portion, which air-inlet portion 4 opens into the testing chamber 6, while provided with an air-outlet portion 9 at the other end portion, i.e., at a rear end portion thereof, which air-outlet portion 9 is connected with an air-intake duct 10 provided with an air-conditioning unit 11. Air cooled in the air-conditioning unit 11 is driven by a fan 12 so as to be horizontally fed into the testing chamber 6 from a lower air-discharging opening 13a of an air-discharging duct 13 which is provided in a rear portion of the interior of the testing apparatus's main frame 1, and which is connected with the air-intake duct 10.

Incidentally, the reference numeral 14 denotes an automobile which is an article to be tested.

In the humid-environmental testing apparatus of this embodiment of the present invention, the air conditioned in temperature and humidity to predetermined conditions in the air-conditioning unit 11 is fed into the testing chamber 6 through the air-discharging duct 13; a mist 7 is sprayed into chamber 6 by means of a nozzle 8, so as to make the air confined in the testing chamber 6 humid. The air fed into the testing chamber 6 controls the temperature of the automobile 14 and is then sucked into the ceiling ducts 4a, 4b through their air-inlet portions 4 so as to be returned to the air-conditioning unit 11.

In performing the humid-environmental test of automobile 14 in testing chamber 6, as shown in FIG. 2, moisture contained in the air is condensed into water droplets 15 along surfaces of the oblique indoor-ceiling boards 2a, 2b and inner surfaces of the ceiling ducts 4a, 4b. The thus produced water droplets 15 flow down along the surfaces of the oblique indoor-ceiling boards 2a, 2b in opposite directions of the testing chamber 6 so as to flow down along the walls of the testing chamber 6 through the drainage holes 5.

In addition, the water droplets 15 produced in the inner wall surfaces of the ceiling ducts 4a, 4b flow along back-surfaces, i.e., upper surfaces of the oblique indoor-ceiling boards 2a, 2b and the inner wall surfaces of the testing apparatus's main frame 1, so as to also flow down along the walls of the testing chamber 6 through the drainage holes 5.

Figure 3:
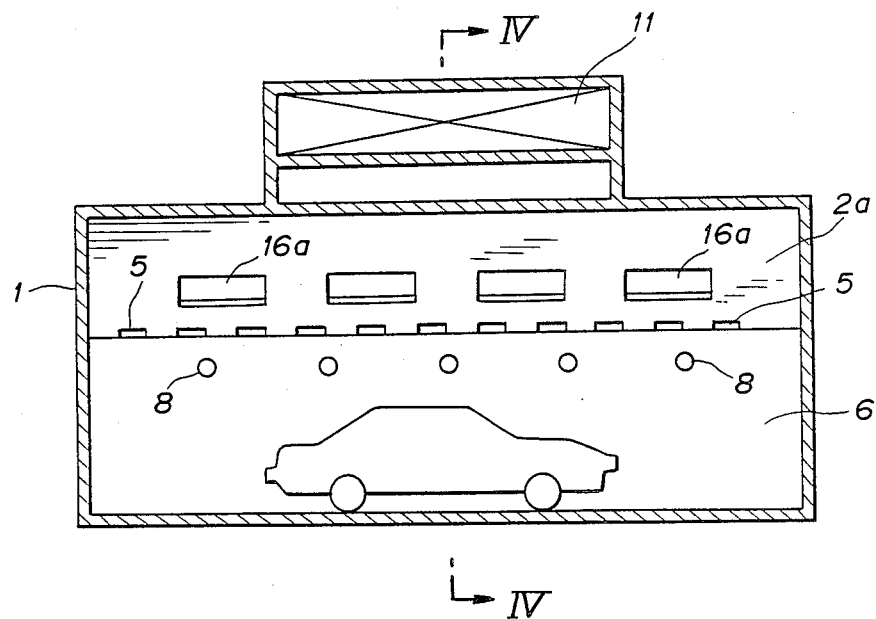
FIG. 3 is a longitudinal sectional view of another embodiment of the humid-environmental testing apparatus of the present invention.
Figure 4:
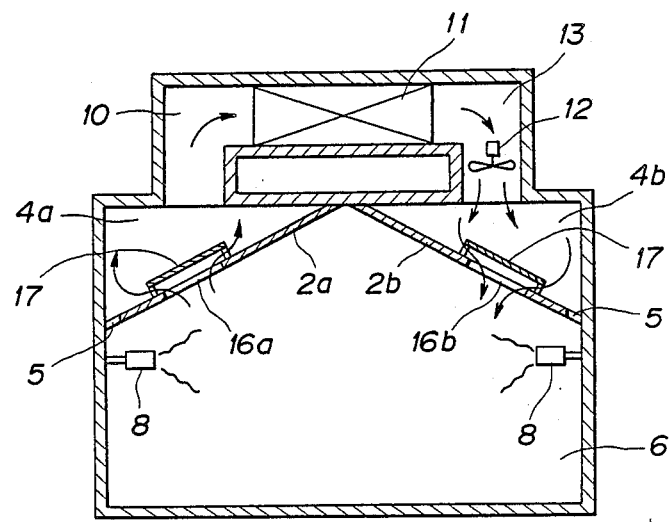
FIG. 4 is a cross-sectional view of another embodiment of the apparatus taken along line IV—IV of FIG. 3.

FIGS. 3 and 4 show a second embodiment of the humid-environmental testing apparatus of the present invention, in which testing apparatus the air-conditioning unit 11 is disposed in an upper portion of the testing apparatus's main frame 1; under the air-conditioning unit 11 are provided the oblique indoor-ceiling boards 2a, 2b, under which is defined the testing chamber 6 in the testing apparatus's main frame 1. Boards 2a and 2b are provided with through-holes 16a and 16b, respectively. Between the oblique indoor-ceiling board 2a and a ceiling portion of the testing apparatus's main frame 1 is formed the ceiling duct 4a, which is communicated with the inlet portion of the air-conditioning unit 11 through the air-intake duct 10, while the ceiling duct 4b opposite to ceiling duct 4a communicates with the outlet portion of the air-conditioning unit 11 through the air-discharging duct 13 in which the fan 12 is provided.

Incidentally, a baffle plate 17 is provided over each of the through-holes 16a, 16b for preventing the water droplets 15 from dropping onto the automobile 14. The remaining construction of this second embodiment of the present invention is the same as that of the first embodiment of the present invention shown in FIGS. 1 and 2.

As shown in FIGS. 3 and 4, in this second embodiment of the present invention, the air issued from the air-conditioning unit 11 passes through the ceiling duct 4b and the through-holes 16b, and then enters the testing chamber 6. The thus entered air in the testing chamber 6 passes through the through-holes 16a and the ceiling duct 4a opposite to the ceiling duct 4b, and is then sucked by the air-conditioning unit 11 through the air-intake duct 10. The water droplets 15 produced in the inner surfaces of the ceiling ducts 4a, 4b and the ceiling surface of the testing chamber 6 flow down along the oblique indoor-ceiling boards 2a, 2b and further flow down through the drainage holes 5 along the walls of the testing chamber 6.

Figure 5:
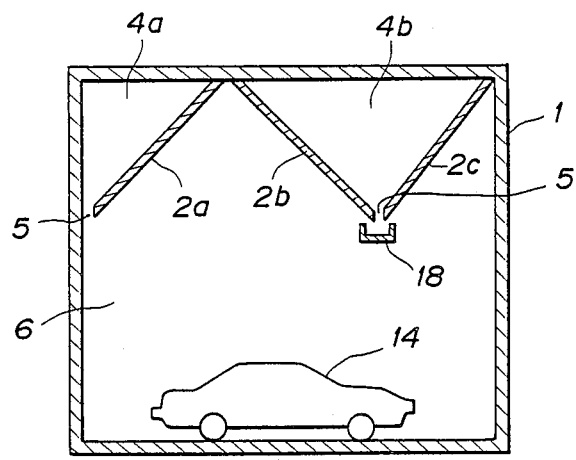
FIG. 5 is a cross-sectional view of the further embodiment of the humid-environmental testing apparatus of the present invention, similar to FIG. 4.

Incidentally, as shown in FIG. 5, it is also possible to construct the oblique indoor-ceiling boards 2a, 2b and 2c in a zigzag-arranging manner to provide one or more drainage holes 5 in a root area defined between the oblique indoor-ceiling boards 2b and 2c, under which drainage holes 5 is provided a gutter 18 which acts as the drainage collection means.

Figure 6:
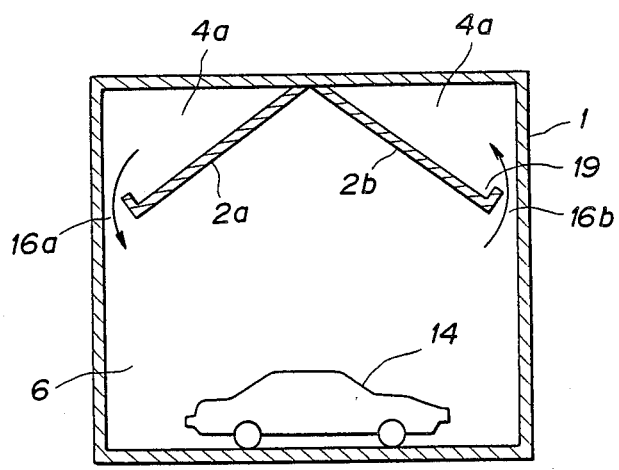
FIG. 6 is a cross-sectional view of still another embodiment of the humid-environmental testing apparatus of the present invention, similar to FIG. 4.

In addition, as shown in FIG. 6, it is also possible to bend a lower end portion of each of the oblique indoor-ceiling boards 2a, 2b upwardly in order to form a gutter 19, so that both the air-outlet 16a and air-inlet 16b portions of the ceiling ducts 4a and 4b are formed in areas adjacent to the lower end portions of the oblique indoor-ceiling boards 2a and 2b, respectively.

In the above embodiments of the present invention, even when a substantially saturated humid atmospheric condition is produced in the testing chamber 6, it is possible to prevent the water droplets 15 from dropping on the automobile 14, so that the automobile 14 can be kept in an accurate-humidity condition so as to increase accuracy in measurement of the environmental testing of automobile 14.

In addition, in the embodiments of the present invention, since the spaces defined between the ceiling portion of the testing apparatus's main frame 1 and the oblique indoor-ceiling boards 2a, 2b form the ceiling ducts 4a, 4b, there is no need to separately provide ceiling ducts, so that it is possible to effectively utilize the interior space of the testing apparatus's main frame 1 and to thereby simplify the whole testing apparatus of the present invention in construction.

What is claimed is:

1. A testing apparatus for determining the corrosion resistance to humidity of a self-propelled vehicle in an enclosed testing chamber, said apparatus comprising:
    (a) an enclosure comprising a frame having a bottom wall, opposed side walls, and an upper wall;
    (b) at least two oppositely disposed, obliquely inclined, indoor ceiling boards, each of said ceiling boards having one end attached to said upper wall of said frame;
    (c) at least two ceiling ducts, each of said ceiling ducts being defined by at least one of said boards and said upper wall of said frame, one of said ceiling ducts further comprising an air outlet for conducting air outwardly from said one ceiling duct;
    (d) an air intake duct provided in an air conditioning unit which is attached to said frame, said air intake duct being attached to said air outlet of said one of said ceiling ducts;
    (e) an air discharge duct for said air conditioning unit which is fluidly attached to said air intake duct, said air discharge duct comprising means for conducting air from said air conditioning unit towards said testing chamber;
    (f) an air discharge opening which opens into said testing chamber, wherein said testing chamber is formed between said bottom wall of said frame and said ceiling boards; and
    (g) means for draining liquid from said ceiling duct, said liquid draining means being located along a lower edge portion of each of said ceiling boards.

2. The testing apparatus of claim 1, wherein said liquid draining means comprises at least one drainage hole provided in each of said obliquely positioned indoor ceiling boards.

3. The testing apparatus in accordance with claim 1, further comprising a drainage gutter positioned beneath at least one of said lower edge portions.

4. The testing apparatus in accordance with claim 1, wherein a first one of said ceiling ducts is fluidically connected to said air conditioning air intake duct.

5. The testing apparatus of claim 4, wherein there are three obliquely inclined indoor ceiling boards, two of said ceiling boards being positioned adjacent each other, wherein said two ceiling boards and said upper surface of said frame define a second one of said ceiling ducts which is connected to said air discharge duct.

6. The testing apparatus in accordance with claim 1, wherein each of said ceiling boards includes a through hole.

7. The testing apparatus in accordance with claim 6, further comprising a baffle plate attached to each of said ceiling boards and positioned over said respective through holes, wherein said baffle plate comprises means for receiving water droplets from said upper wall of said frame.

8. The testing apparatus in accordance with claim 1, comprising three ceiling boards, wherein one of said ceiling boards defines, together with a portion of one of said frame side walls and a portion of said frame upper wall, one of said ceiling ducts, and wherein second and third ceiling boards define, together with a portion of said upper frame wall, a second ceiling duct.

9. The testing apparatus in accordance with claim 1, wherein each of said ceiling boards has a lower edge comprising an upturned flange.

* * * * *

UNITED STATES PATENT AND TRADEMARK OFFICE
CERTIFICATE OF CORRECTION

PATENT NO. : 4,779,468

DATED : October 25, 1988

INVENTOR(S) : Teruaki SUZUKI

It is certified that error appears in the above-identified patent and that said Letters Patent is hereby corrected as shown below:

At column 4, line 52, change "duct" to ---ducts---.

At column 5, line 10, change "receving" to ---receiving---.

Signed and Sealed this

Third Day of July, 1990

Attest:

HARRY F. MANBECK, JR.

Attesting Officer

Commissioner of Patents and Trademarks